United States Patent [19]
Horber

[11] Patent Number: 4,769,039
[45] Date of Patent: Sep. 6, 1988

[54] TIBIAL IMPLANT FOR A KNEE PROSTHESIS

[75] Inventor: Willi Horber, Zurich, Switzerland

[73] Assignee: Sulzer Brothers Limited, Winterthur, Switzerland

[21] Appl. No.: 900,702

[22] Filed: Aug. 27, 1986

[30] Foreign Application Priority Data

Sep. 12, 1985 [CH] Switzerland .................. 3939/85

[51] Int. Cl.⁴ .................................. A61F 2/38
[52] U.S. Cl. .................................. 623/20
[58] Field of Search ............ 623/11, 16, 20, 18, 623/22, 23

[56] References Cited

U.S. PATENT DOCUMENTS 4,568,348 2/1986 Johnson .......................... 623/20

FOREIGN PATENT DOCUMENTS

| 0151724 | 8/1985 | European Pat. Off. | 623/20 |
| 2905592 | 8/1979 | Fed. Rep. of Germany | 623/20 |
| 2266492 | 10/1975 | France | 623/20 |
| 2465470 | 4/1981 | France | 623/20 |

Primary Examiner—Richard J. Apley
Assistant Examiner—D. Isabella
Attorney, Agent, or Firm—Kenyon & Kenyon

[57] ABSTRACT

The tibial implant is made with two truncoconical faces which extend from a common plane for different distances. The differential extent permits implantation in a natural tibia having sockets which have different degrees of wear, thus avoiding unnecessary loss of healthy bone during a resection procedure. The truncoconical faces are provided on metal bowls which can be welded together along a common plane and which together form a support to receive a plastic member providing the joint sliding surfaces and providing a pair of expansion elements for expanding barbed hollow bodies extending from the metal bowls.

9 Claims, 2 Drawing Sheets

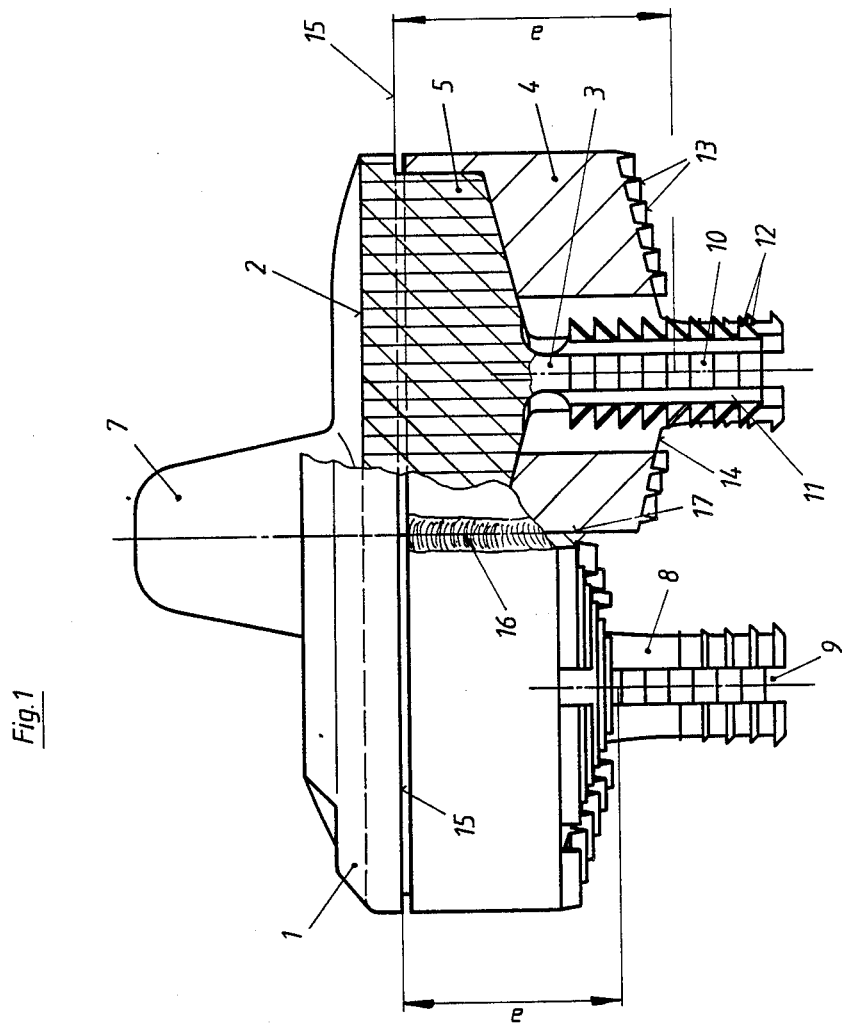

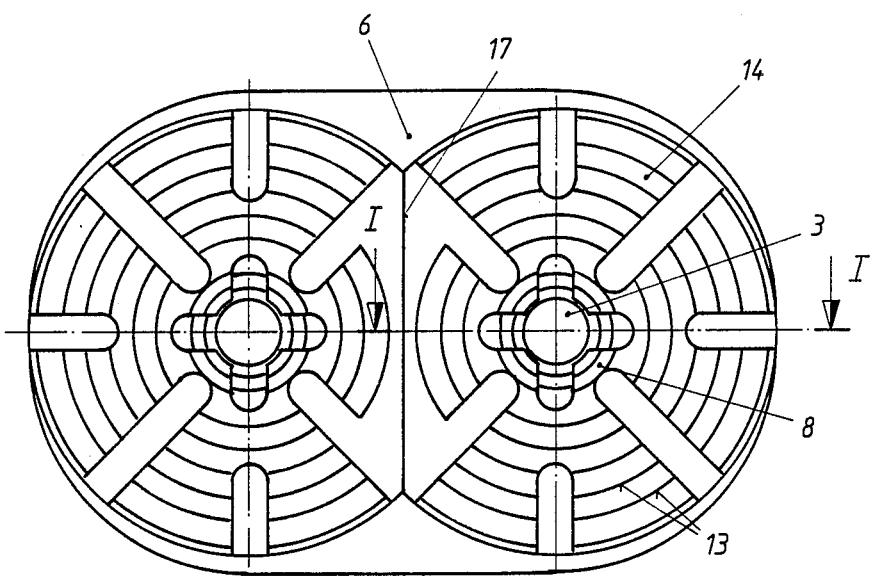

TIBIAL IMPLANT FOR A KNEE PROSTHESIS

This invention relates to a tibial implant for a knee prosthesis.

As described in European Patent Application No. 0151724, tibial implants have been known to employ anchoring pins in order to anchor the implant in a tibia. Further, it has been known to surround each anchoring pin with a truncoconical face which extends obliquely to and concentric with the axis of the pin. However, it has been found in practice that the sliding surfaces of the knee joint sockets on the tibia are often damaged in greatly different degrees. For example, the lateral joint socket may be frayed more than the medial socket or vice versa. In the past, the required bone resection for implanting a tibial implant has depended upon the depth of the greatest destruction in the tibia. Thus, where one joint socket is damaged to a greater degree than the other, it has been necessary to remove healthy bone substance unnecessarily from the joint socket of less damage.

Accordingly, it is an object of the invention to reduce or to avoid entirely the unnecessary loss of healthy bone substance in a natural tibia for an implant.

It is another object of the invention to provide a tibial implant which can adapt to different degress of damage in the joint sockets of a natural tibial plateau.

Briefly, the invention provides a tibial implant for a knee prosthesis which comprises a tibial sliding surface on one side, at least two anchoring pins extending from an opposite side for securement in a tibia and a pair of obliquely extending truncoconical faces. Each face is disposed concentrically of a respective pin and extends perpendicularly from a common reference plane a distance which is different from the other face.

With a tibial implant thus formed, a tibia may be drilled or reamed to different depths for the truncoconical faces in the region of the lateral and medial anchoring pins, respectively, depending upon the amount of damage which is occurred. For example, if the lateral joint socket is damaged to a greater depth than the medial joint socket of a tibia, the lateral joint socket can be subject to a deeper resection of bone in order to receive the larger truncoconical face.

The tibial implant thus avoids any need to resect healthy bone issue of a tibia unnecessarily.

In order to simplify manufacture, the tibial implant is made of two members. One member is provided with the sliding surface while the second member is provided with the truncoconical faces as well as a recess for receiving the first member. Further, the second member may include a pair of circular cylindrical truncoconical elements formed at the sides with flat faces which abut and are integrally secured together. In this case, the first member includes a pair of circular cylindrical projections which are received in a pair of mating recesses in the second member as well as a pair of expansion elements each of which extend coaxially from a cylindrical projection through the second member and into a split hollow body extending from a truncoconical element of the second member to expand the hollow body. Each hollow body and the received expansion element may be appropriately shaped to form a closed anchoring pin for a substantially uniform ingrowth of tissue.

In order to provide for enhanced sliding properties, the member having the tibial sliding surface thereon may be made, at least in part of a plastic such as polyethylene. However, the tibial implant members may be made of any of the known implant materials, such as metals, metal alloys, bioceramic materials, carbon or fiber reinforced composite materials or from two or more of these materials, particularly where one member is made of metal and the other member is made of plastic. In addition, the surfaces of the implant may be provided wholly or partly with bioinert or bioactive coatings.

These and other objects and advantages of the invention will become more apparent from the following detailed description taken in conjunction with the accompanying drawings wherein:

FIG. 1 illustrates an interior/posterior view of a tibial implant according to the invention taken, in part, on line I—I of FIG. 2; and FIG. 2 illustrates a bottom view of the tibial implant of FIG. 1.

Referring to FIG. 1, the tibial implant is made of two-parts consisting of metal and plastic. In this regard, the implant includes a plastic member 1 which contains tibial sliding surfaces or joint sockets 2. In addition, the member 1 has a pair of circular cylindrical projections 5 extending away from the sliding surface and a pair of expansion elements 3 each of which extends coaxially from a respective projection 5. As shown in FIG. 1, each projection 5 has a conically extending bottom and, as indicated in FIG. 2, each projection 5 extends from a tibia plateau 6 which faces toward the bone.

The sliding surfaces 2 function to receive condyloid counter surfaces of a femur part (not shown) in a manner so that the femur part can roll off in a slidable manner. In addition, a guide pin 7 is located between the sliding surfaces 2 in order to guide the femur part (not shown ) during a sliding roll-off movement.

Each expansion element 3 which extends from a projection 5 has teeth-like projections 10 and longitudinal cut-outs 11 between each row of teeth 10.

Referring to FIG. 1, the second member of the implant is in the form of a metal support 4 which has a pair of trough or bowl-like recesses shaped to receive the projections 5 of the plastic member 1. In this regard, the support 4 may be formed of two circular-cylindrical metal bowls which have flat faces 17 abutting andintegrally secured together as by a weld seam 16.

In addition, each metal bowl is provided with an obliquely extending truncoconical face 14 on the bottom which is covered by a plurality of cutting edge type ribs 13. As indicated in FIG. 2, the ribs are disposed in concentric rings with relief areas formed by radially disposed slots which improve the stability against rotary loads.

As indicated in FIG. 1, the truncoconical surface 14 shown to the right of FIG. 1 extends perpendicularly from a common plane 15 of the tibia plateau 6 a greater distance a than the other truncoconical face 14. As indicated in FIG. 1, the common plane 15 may correspond with the lower edge of the tibial plateau 6. Alternatively, the plane 15 may correspond to the upper edge of the metal support 4.

The support 4 also has a pair of hollow bodies 8 each of which is coaxially of and extends from a respective truncoconical face 14 in order to receive an expansion element 3 therein. Each hollow element 8 is formed with longitudinal slits 9 and alternating individual strips which are provided with barb-like ribs 12. When the implant is assembled, the expansion elements 3 pass through the hollow bodies 8 to form a dowel type anchoring. During this time, the expansion elements 3 widen the walls of the hollow bodies 8.

Each expansion element 3 is in the form of a "negative" of a hollow body 8 in which the element 3 is received. In this respect, the projecting teeth on the element 3 are aligned with the longitudinal slits 9 of the hollow body 8 while the longitudinal cut-outs 11 are aligned with the ribbed strips of the hollow body 8. When implanted in a cement-free anchoring, the expansion elements 3 and hollow bodies 8 form "closed pins" onto which and into which tissue can grow evenly on all sides.

In order to fabricate the tibial implant, appropriate dimensions are selected for each of the metal bowls which are to form the support 4. The bowls are then welded together along the flat surfaces 17 which extend parallel to the axes of the expansion elements 3 via a weld seam 16. Thereafter, the plastic member 1 having the pair of expansion elements 3 thereon and which may be of standard size is inserted into the thus formed support 4. In this way, a set of tibial implants can be provided with truncoconical faces of different extents.

Depending upon the extent of damage to the joint sockets of a tibia, an appropriate tibial implant can be selected and the tibia resected in each socket to an appropriate extent to receive the implant without unnecessarily removing healthy bone.

What is claimed is:

1. A tibial implant for a knee prosthesis, said implant comprising
   a tibial sliding surface on one side;
   at least two anchoring pins extending from an opposite side for securement in a tibia; and
   a pair of obliquely extending truncoconical faces on said opposite side, each said face being disposed concentrically of a respective pin and extending perpendicularly from a common reference plane a distance different from the other of said pair of faces to permit limited resection of a tibia for implanting the implant.

2. A tibial implant as set forth in claim 1 further comprising a first member having said sliding surface thereon and a second member having said faces thereon and a recess receiving said first member therein.

3. A tibial implant as set forth in claim 2 wherein said second member includes a pair of circular cylindrical truncoconical elements having flat faces abutting and integrally secured together.

4. A tibial implant as set forth in claim 1 comprising a first member having said sliding surface thereon and including a pair of circular cylindrical projections extending towards said opposite side and a pair of expansion elements, each expansion element being concentric to a respective projection and said second member having said truncoconical faces thereon and including a pair of recesses respectively receiving said projections and a pair of expandable hollow bodies respectively receiving said expansion elements.

5. A tibial implant as set forth in claim 4 wherein each said hollow body and a received expansion element defines a closed anchoring pin.

6. A tibial implant as set forth in claim 4 wherein said first member is made of plastic and said second member is made of metal.

7. A tibial implant for knee prosthesis comprising
   a first member having a tibial sliding surface on one side, a pair of projections extending towards an opposite side and a pair of expansion elements, each element extending from a respective projection; and
   a second member having a pair of recesses respectively receiving said projections, a pair of obliquely extending truncoconical faces, each face extending perpendicularly from a common reference plane a distance different from the other face and a pair of hollow bodies, each hollow body being concentric to and extending from a respective truncoconical face and receiving a respective expansion element therein.

8. A tibial implant as set forth in claim 7 wherein said second member includes a pair of circular cylindrical truncoconical elements having flat faces abutting and integrally secured together.

9. A tibial implant as set forth in claim 7 wherein said first member is made of plastic and said second member is made of metal.

* * * * *

UNITED STATES PATENT AND TRADEMARK OFFICE
CERTIFICATE OF CORRECTION

PATENT NO. : 4,769,039
DATED : September 6, 1988
INVENTOR(S) : Willi Horber

It is certified that error appears in the above-identified patent and that said Letters Patent is hereby corrected as shown below:

Column 1, line 41 change "is" to -has-

Column 1, line 47 change "issue" to -tissue-

Column 2, line 20 change "two-parts" to -two parts-

Column 2, line 44 change "andinte-grally" to -and inte-grally-

Column 2, line 62 change "coaxially" to -coaxial-

Signed and Sealed this

Fourteenth Day of February, 1989

Attest:

DONALD J. QUIGG

Attesting Officer

Commissioner of Patents and Trademarks